US006587598B1

(12) United States Patent
Devillers et al.

(10) Patent No.: US 6,587,598 B1
(45) Date of Patent: Jul. 1, 2003

(54) IMAGE PROCESSING METHOD, SYSTEM AND APPARATUS FOR FORMING AN OVERVIEW IMAGE OF AN ELONGATED SCENE

(75) Inventors: Sylvain Devillers, Paris (FR); Shérif Makram-Ebeid, Dampierre (FR); Steven Lobregt, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/507,401

(22) Filed: Feb. 18, 2000

(30) Foreign Application Priority Data

Feb. 18, 1999 (EP) ............................................. 99400399

(51) Int. Cl.⁷ ................................................. G06K 9/36
(52) U.S. Cl. ........................ 382/284; 382/130; 382/132; 382/294
(58) Field of Search ................................. 382/284, 130, 382/132, 294; 351/206; 378/98; 342/179

(56) References Cited

U.S. PATENT DOCUMENTS

| | | | | |
|---|---|---|---|---|
| 6,078,699 A | * | 6/2000 | Lobregt et al. | 382/284 |
| 6,081,582 A | * | 6/2000 | Mazess et al. | 378/146 |
| 6,097,833 A | * | 8/2000 | Lobregt et al. | 382/130 |

FOREIGN PATENT DOCUMENTS

| | | | | |
|---|---|---|---|---|
| EP | 0737940 A2 | * 10/1996 | ............ | G06T/11/00 |
| EP | 0861556 A2 | 9/1998 | ............ | H04N/5/32 |
| WO | 9808338 | 2/1998 | ............ | H04N/5/32 |
| WO | WO9808338 | 2/1998 | ............ | H04N/5/32 |
| WO | 9906943 | 2/1999 | ............ | G06K/9/32 |

OTHER PUBLICATIONS

Steven Lobregt et al., "A Discrete Dynamic Contour Model", IEEE Transactions on Medical Imaging, Mar. 1995, vol. 14, No. 1, pps. 12–24.*
By L.R. Rabiner and B.H. Juang, Entitled: "An Introduction to Hidden Markov Models", In IEEE ASSP Magazine, Jan. 1986, p. 11, Box 2.

* cited by examiner

Primary Examiner—Anh Hong Do
(74) Attorney, Agent, or Firm—John Vodopia

(57) ABSTRACT

The invention relates to an image processing method with steps of acquiring (1) a sequence of translation overlapping images (11) representing an elongated scene; determining regions (ROI) in image pairs (Pk) and region sections (Bj) having dimensions suitable for matching (2); estimating region and section displacement fields (24, 25); regularizing (3) said region and section displacement fields (34, 35); interpolating pixel values of sections that have dimensions suitable for merging calculated from the regularized section displacement field, so as to evaluate the pixel values of corresponding regions and further scaling the sections in said regions to dimensions calculated from the regularized region displacement field, and reconstructing (4) an overview image (41) of the elongated scene (112) with said regions. The invention also relates to a system for implementing said method and a medical examination apparatus having said image processing system.

18 Claims, 8 Drawing Sheets

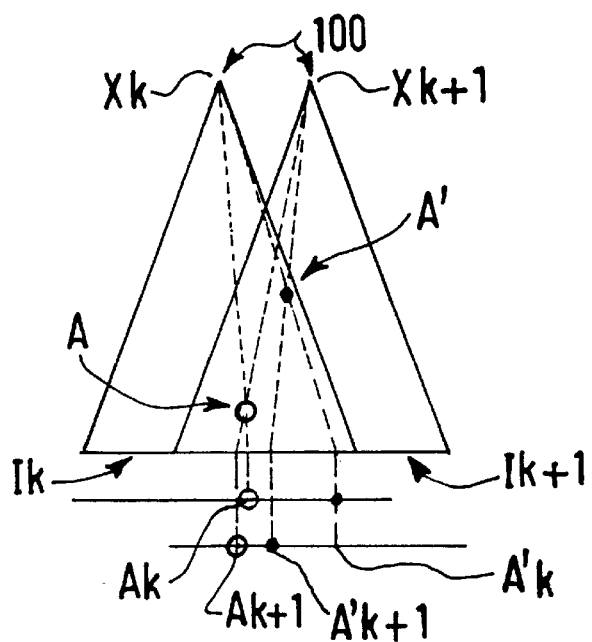
FIG.3A
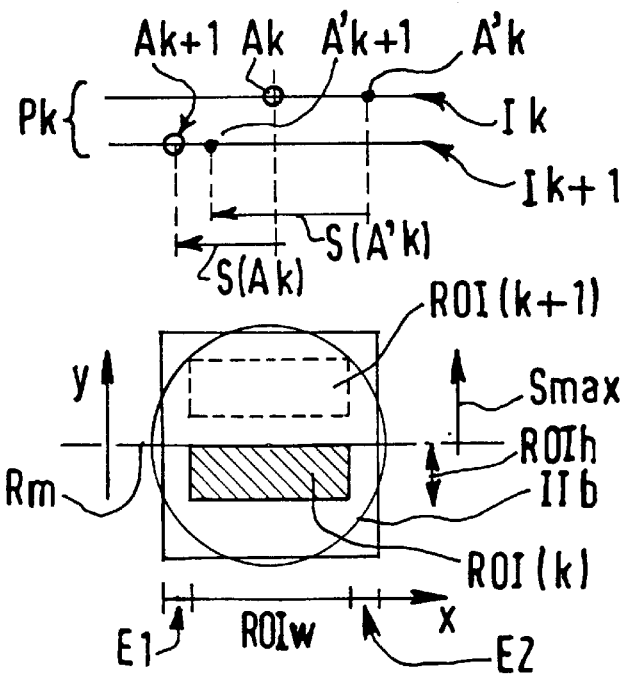
FIG.3B
FIG.4A
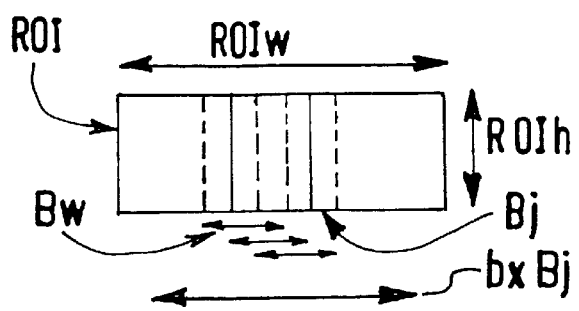
FIG.4B

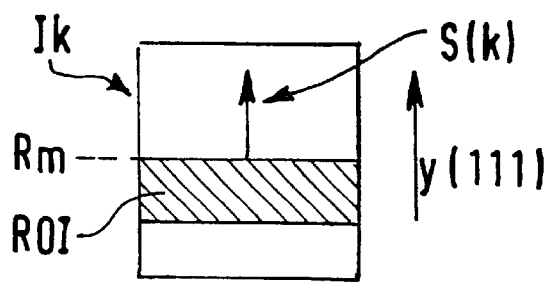
FIG.5A
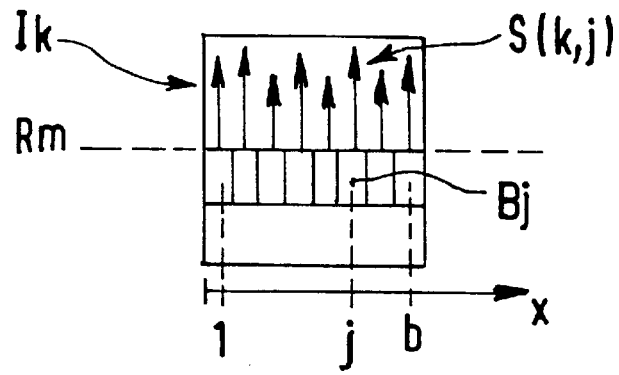
FIG.5B
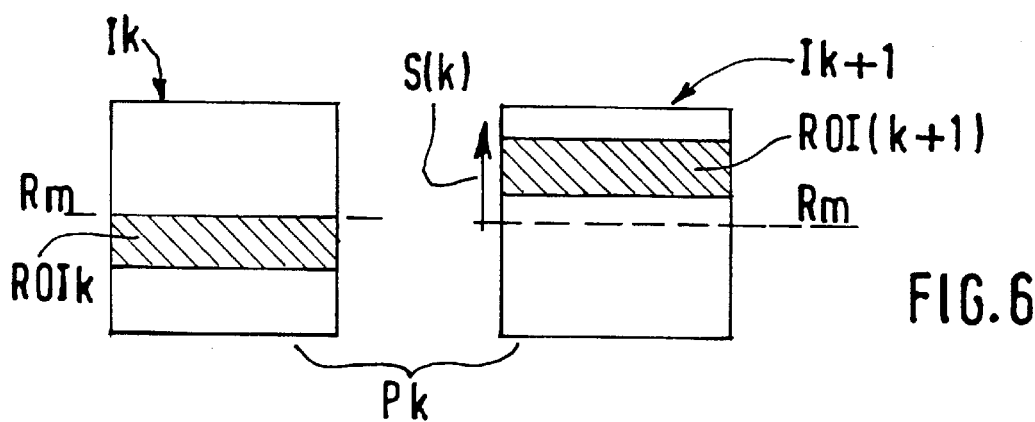
FIG.6
FIG.7A
FIG.7B
FIG.7C
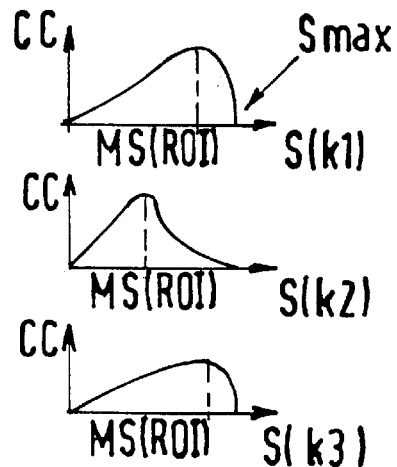

IMAGE PROCESSING METHOD, SYSTEM AND APPARATUS FOR FORMING AN OVERVIEW IMAGE OF AN ELONGATED SCENE

FIELD OF THE INVENTION

The invention relates to an image processing method comprising steps of acquiring a sequence of overlapping images representing an elongated scene and steps of merging said images into an overview image.

The invention also relates to an image processing system to perform said method. The invention further relates to an X-ray apparatus comprising an image processing system for performing said method.

The invention finds its application in the field of medical apparatus.

In medical X-ray imaging it is necessary to form images of large areas, notably X-ray images of blood vessels in the limbs in the field of peripheral X-ray angiography, or spinal column images, or complete region radiography of an arm or a leg of a patient. Using a standard X-ray apparatus at the present time, it is difficult to form images of such large regions in one exposure. Generally, a sequence of successive X-ray images of zones of the region to be examined is formed in such a manner as to cover the entire region.

BACKGROUND OF THE INVENTION

Such an image processing method is already known from European Patent Application EP 0861556, published under the PCT reference number WO98/08338. This document discloses a method of forming an overview image of an elongated scene which is too long to be imaged by acquiring only a single standard image. The overview image is formed by merging successive overlapping images of an image sequence of the elongated scene while using steps of combining image pairs on the basis of their individual shift. The images may be X-ray images formed by irradiating a patient by means of an X-ray beam in different positions.

According to the cited document, the elongated scene comprises a first and a second kind of object which are constituted by a ruler and by elongated anatomical structures respectively. The two kinds of objects being situated at different distances from the X-ray source, they are imaged in the overlapping images with parallax artefacts. To solve this problem, the known method comprises steps of separately processing first and second portions of the image, representing the ruler and the anatomical structures respectively. First and second shift values are derived from an image pair for the first and second image portions which are further combined independently by application of a correlation to their pixel values. The first resultant combined portion, representing the ruler is then either compressed or expanded, taking into account the ratio of the two shift values, in order to provide a parallax corrected combined first portion. A combined image of the image pair is further constructed by sewing the two resultant combined portions together. The overview image is further constructed by combining all the combined images obtained from the image pairs.

In the known method, the first and the second shifts are assumed to be substantially constant within said first and second image portions over the whole sequence, but this assumption is not verified. Parallax occurs because individual parts of the elongated scene are situated at different distances from the X-ray source and are viewed from different positions of the X-ray source either for different objects in the same image or for the same object represented in different overlapping images.

A first problem in the known method is that there are still parallax artifacts in the overview image. This may result in that, in the overview image, reconstructed bones show hachured walls or doubled joints, reconstructed vessels seem doubled or partly disappear and the ruler shows blurred or split graduations.

Another problem of the known method is that it may not be fully automated because the first and second portions of images representing the ruler and the anatomical structures must be selected by visual inspection of the images.

Another problem of the known method is that user interaction is further necessary for determining structures of interest of said first and second portions so as to evaluate the correlation laws and shift values.

Another problem of the known method lies in finding a background zone for operating a boundary sewing of the first and second combined portions side by side, after they have first been processed separately.

SUMMARY OF THE INVENTION

It is an object of the present invention to provide a method, a system and an apparatus for constructing an overview image from a sequence of images, in which parallax effects are counteracted better than in the known method.

This object is achieved by an image processing method comprising steps of acquiring a sequence of overlapping images representing an elongated scene, said images being obtained at different positions along a translation direction, and steps of merging said images into an overview image, including determining regularized displacement fields of overlapping regions of interest (ROI) and sections (Bj) of said regions in image pair and merging said section based on dimensions calculated from the regularized region displacement field. A system of the invention comprises an arrangement of calculation means for carrying out the methods of the invention. An apparatus of the invention comprises acquisition means for acquiring examination images of a patient, translation means for acquiring translation of consecutive overlapping images of an elongated part of the patient, and an image processing system comprising an arrangement of calculation means for carrying of the methods of the invention claim 16.

An advantage of this method is that it improves image quality by reducing parallax artifacts without increasing the acquisition sequence duration and hence the X-ray dose for the patient in the case where the image frames are formed using an X-ray apparatus.

Another advantage of this method is that it does not need user interaction to be performed. It may be performed completely automatically.

Another advantage of this method is that it does not rely on structures of interest to construct the composite image. The image frames may comprise several kinds of objects, such as anatomical objects and rulers, or only one kind of objects such as purely anatomical objects. This method is carried out independently of the nature of objects in the image frames.

Citation of a reference herein, or throughout this specification, is not to construed as an admission that such reference is prior art to the Applicant's invention of the invention subsequently claimed.

BRIEF DESCRIPTION OF THE DRAWINGS

The invention will be described in detail hereafter with reference to diagrammatic figures, wherein:

FIGS. 3A, 3B illustrate the parallax effect in an image pair;

FIGS. 4A, 4B illustrate the definition of ROI block and reference blocks Bj;

FIGS. 5A, 5B illustrate the displacement fields in ROI and reference blocks Bj;

FIG. 6 illustrates the shift of the ROI block in the matching operation;

FIGS. 7A, 7B, 7C show CC curves versus shift amplitude for ROI in image pairs;

DESCRIPTION OF THE PREFERRED EMBODIMENTS

Figure 1A:
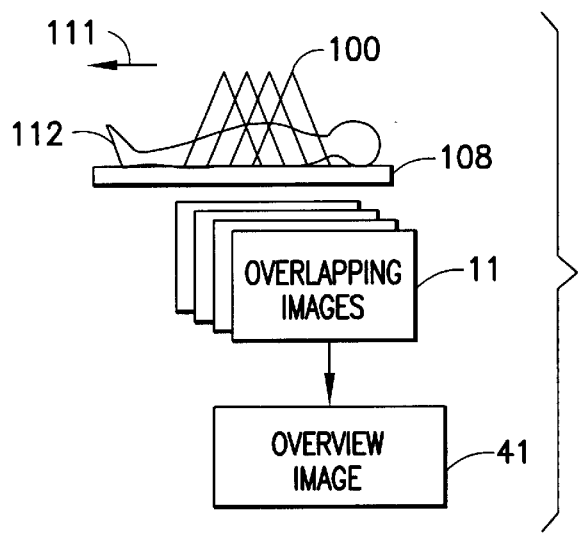
FIG. 1A illustrates the method of the invention.

Referring to FIG. 1A, the invention relates to an image processing method comprising steps of acquiring a sequence of overlapping digital images 11 of an elongated scene, representing an elongated object 112, and steps of reconstructing an overview image 41 from said overlapping images 11. Each overlapping image 11 is obtained at different translation positions of the elongated object 112 with respect to a source 100 coupled to a detector system and represents a part of said elongated object 112. The translation is performed in a translation direction 111. This method may be applied to different kinds of images, such as X-ray images or Magnetic Resonance images, and does not depend on the type of translation images which are acquired.

Figure 1B:
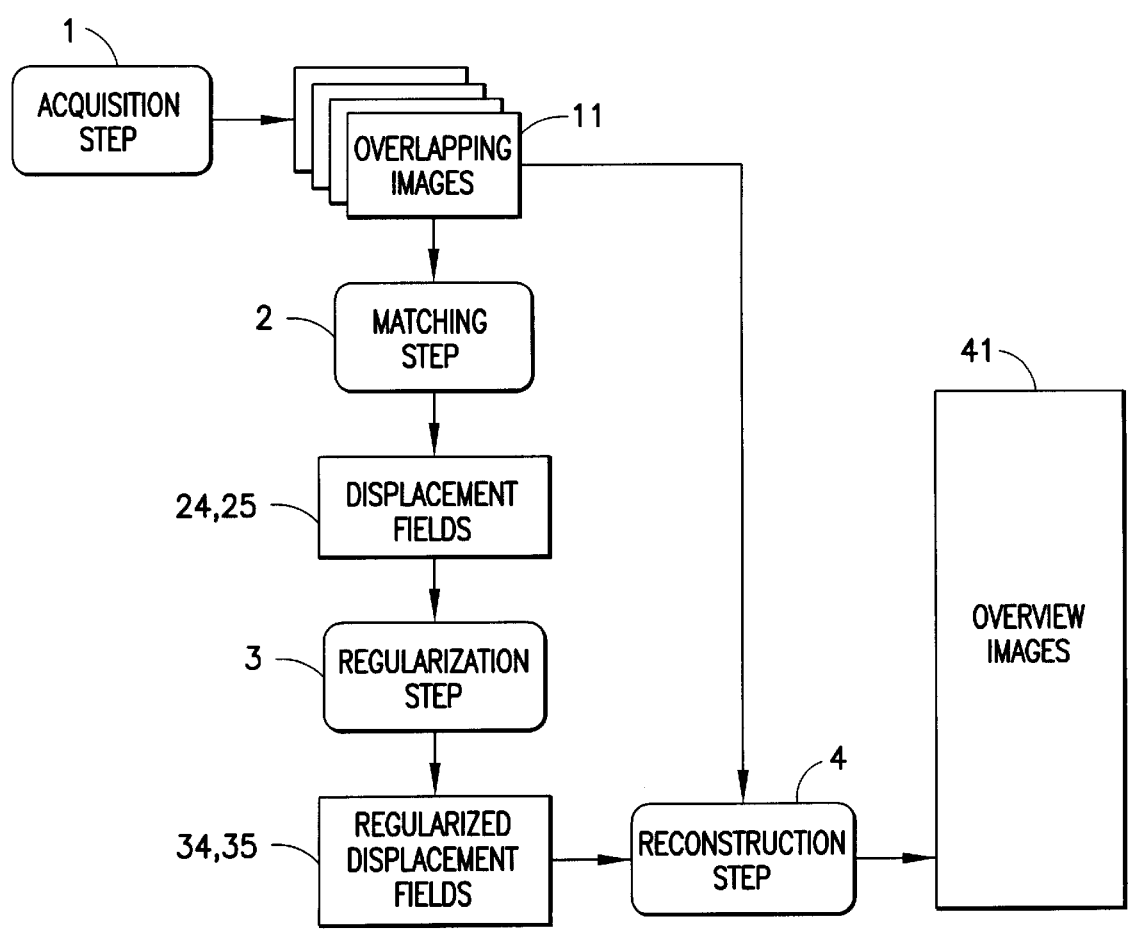
FIG. 1B is a simplified functional block diagram of the main steps of the method and FIG. 1C is a functional block diagram of detailed steps of the method.

FIG. 1B diagrammatically shows main steps of the image processing method comprising an acquisition step 1 for the overlapping image sequence 11, a matching step 2 for estimating displacement fields 24, 25 in image pairs, a regularization step 3 providing regularized displacement fields 34, 35, and a reconstruction step 4 for the overview image 41 representing the elongated scene corrected for parallax errors.

Figure 1C:
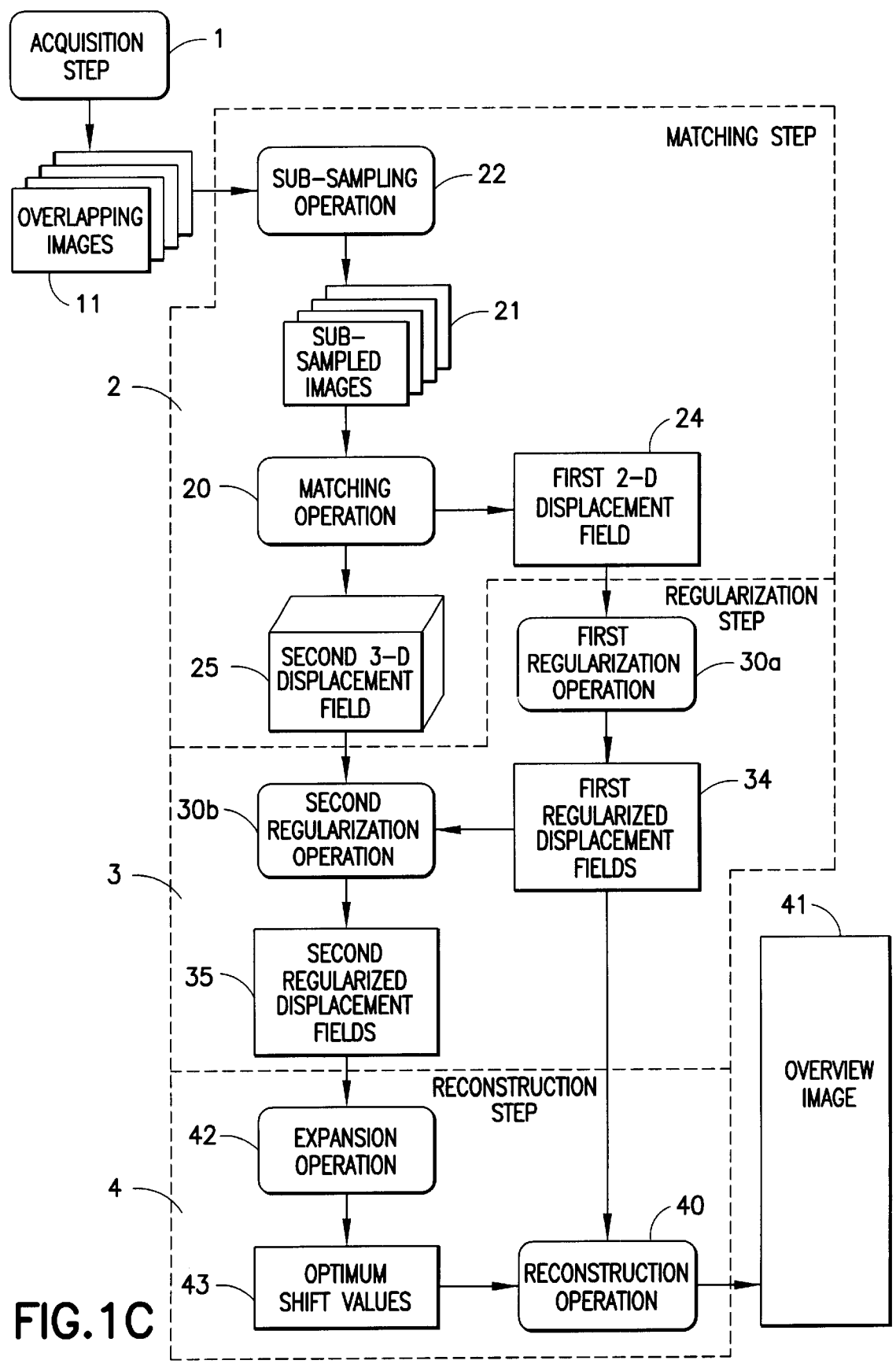

FIG. 1C shows diagrammatically detailed steps of the image processing method. This method may comprise, in the matching step 2, a sub-sampling operation 22 providing a sequence of sub-sampled images 21; a matching operation 20 providing a first 2-D displacement field 24 to estimate apparent shifts of Regions Of Interest defined in image pairs, and a second 3-D displacement field 25 to estimate apparent shifts of Reference Blocks defined in said Regions Of Interest in the image pairs. This method further comprises first and second regularization operations 30a, 30b which provide first and second regularized displacement fields 34, 35 and derive respective optimum shift values. This method furthermore includes an expansion operation 42 to evaluate optimum shift values 43 applied to the original images, derived from the displacement field 35; a reconstruction operation 40, based on said optimum shift values 43 and 34, provides the overview image 41.

Figure 2A:
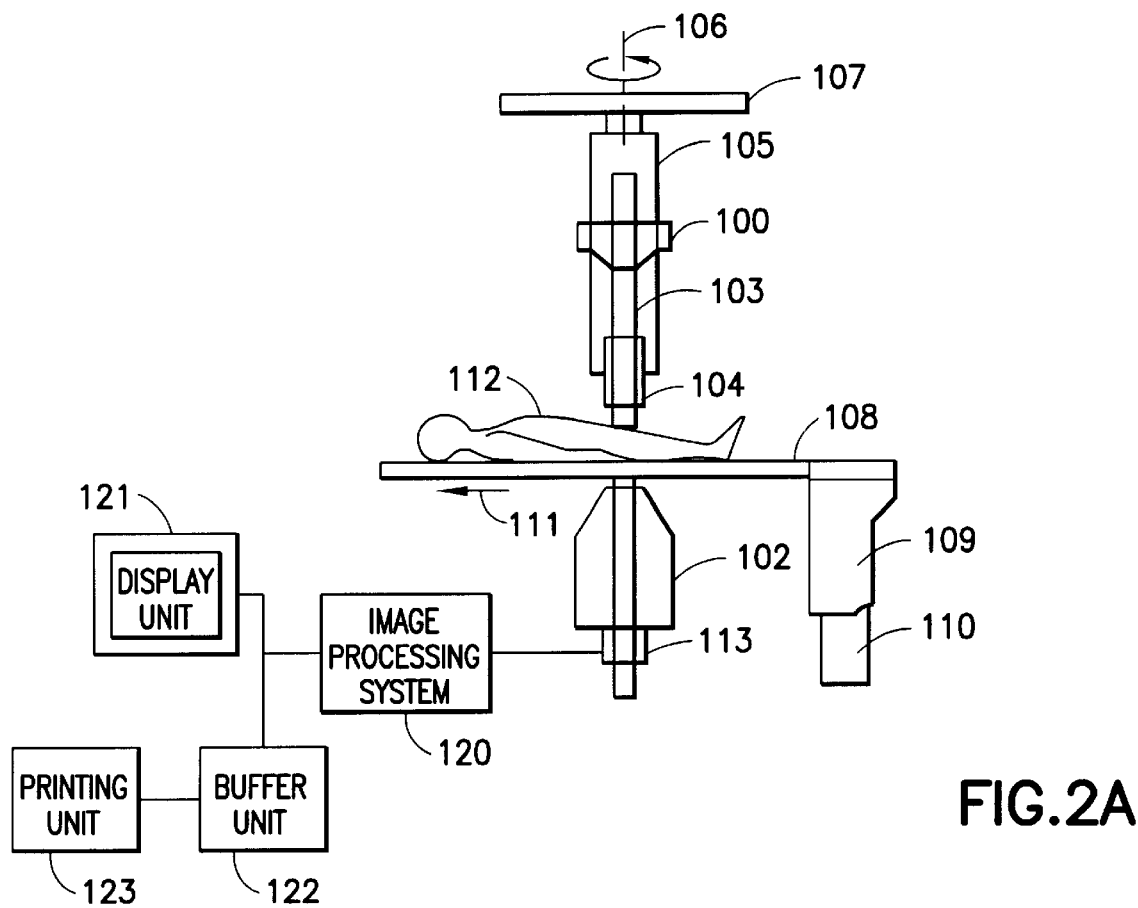
FIG. 2A illustrates an X-ray apparatus with processing means and FIG. 2B illustrates image formation by said means.

Referring to FIG. 2A, the acquisition step 1 may be carried out while using an X-ray apparatus. FIG. 2A is a side elevation of an X-ray examination apparatus for forming X-ray images of a patient 112. An X-ray source 100 and an X-ray detector 102, for example an image intensifier, are connected to a carrier 103, for example a C-arm, which is movably connected to a vertical support 105 by means 104. The vertical support 105 may be rotated around an axis 106 and is suspended from fixed rails 107. A frame 109 may be moved along a column 110 to adjust the height of a connected patient table 108 with respect to the X-ray source. The frame 109 also enables translation of the patient table 108 in the longitudinal direction 111 relative to the X-ray source 100. In this configuration, the patient 112 is disposed on the patient table 108. It is alternately possible for the patient to stand upright during the examination, the frame 109 with the X-ray source and detector being vertically movable along the patient. For each separate position resulting from a translation step, an X-ray image is formed by irradiating a part of the patient 112 so as to constitute a sequence of overlapping images 11. In the images, the translation direction 111 is parallel into the columns of pixels along a y-axis of coordinates, whereas the rows of pixels are parallel with an x-axis of coordinates. Local differences in X-ray absorption within the patient permit to form X-ray shadow images on an entrance screen of the image intensifier 102. Optical images are derived on an exit window and picked up by a video system 113, which supplies electronic video signal levels that represent digital brightness values of said images. Individual images form a sequence of overlapping images 11 which are further combined according to the invention in order to reconstruct the overview image 41. To that end, the image signals of each image are applied to an image processing system 120, which merges said images to form image signals of the overview image 41. The image processing system 120 may be coupled to a display system 121 and to a printing unit 123 via a buffer unit 122. The image processing system 120 may be a suitably programmed computer, or a special-purpose processor having circuit means that are arranged to perform the finctions of the method steps according to the invention.

Figure 2B:
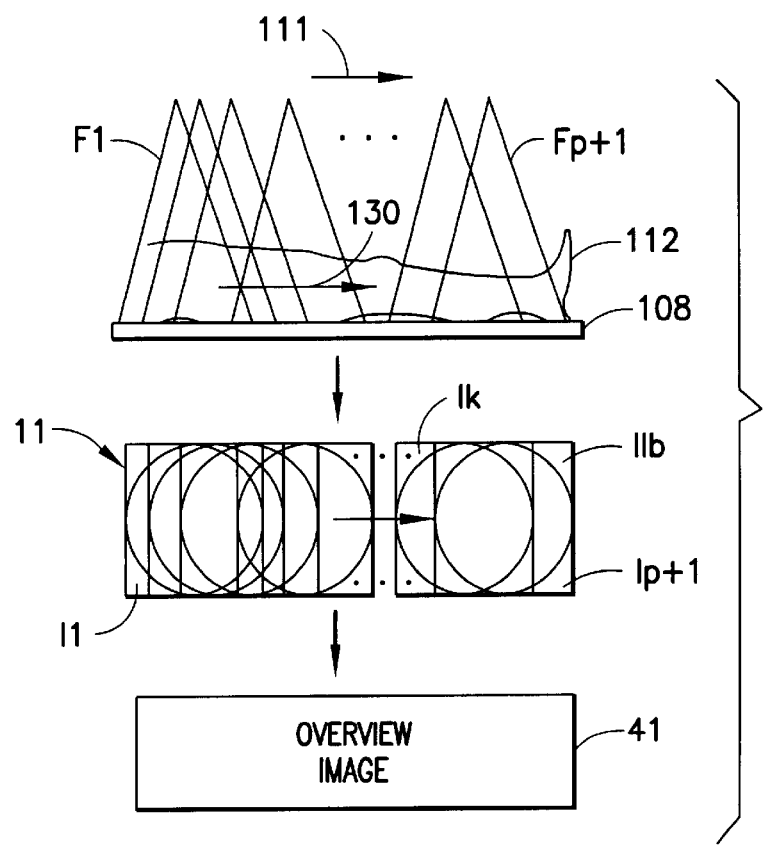

Referring to FIG. 2B, overlapping digital images referred to as Ik, where k is an integer from 1 to p+1, are formed at separate mutual positions during the translation of the patient 112 relative to the X-ray source 100. The images Ik have a border denoted IIb due to the shape of the image intensifier 102. The elongated scene 112 to be reconstructed as an overview image 41 may comprise anatomical structures such as bones and the vascular system of a patient limb, or the spinal column, and occasionally a ruler with scale graduations. So the sequence of X-ray images 11 may contain image information concerning said anatomical structures and, occasionally, said ruler structure. The image information in the single overview image 41 is more readily available for diagnosis than the individual images 11.

Referring to FIG. 1C, during the matching operation 20, the images of the sequence 11 are considered in pairs of successive images having an overlapping zone. Referring to FIG. 3A, an image pair referred to as Pk comprises a source image, denoted Ik, and a subsequent target image, denoted Ik+1. The total number of images is p+1, so the total number of image pairs is p. The matching operation 20 provides arrays 24, 25 of shift values for each image pair, and further for the whole image sequence.

FIG. 3A illustrates the formation of parallax artifacts which are counteracted when the method of the invention is used. The source 100 is set in a first and then in a second position Xk, Xk+1 and emits first and second beams Fk, Fk+1 which form first and second overlapping shadow images Ik, Ik+1 of the elongated object respectively. An actual point A disposed at a first height in the elongated object is imaged at a point Ak in the shadow image Ik and at a point Ak+1 in the subsequent shadow image Ik+1. Another actual point A' disposed at a different height in the elongated object is imaged at a point A'k in the shadow image Ik and at a point A'K+1 in the subsequent shadow image Ik+1.

Referring to FIG. 3B, the respective distances between Ak and AK+1 and between A'K and A'K+1 are not equal. So, two points situated at different heights in the elongated object have two different shift values S(k, A) and S(k, A') in this image pair Pk, which results in the occurrence of parallax artifacts. The steps 2 and 3 of the invention have for their aim to counteract the occurrence of parallax artifacts.

Referring to FIG. 4A, a Region of Interest for matching referred to as ROI block is estimated in a pair Pk of images. The ROI is defined as a zone of the first image Ik of the pair Pk whose upper border coincides with the medial row Rm. The height ROIh of the ROI is chosen to be a value that corresponds to the application, such as, for example, ROIh= 80 pixels for peripheral angiography images of the legs, ROIh=64 pixels for spine images which roughly corresponds to the distance between two ribs, so that the ROI blocks defined in the thoracic region contain at least one rib edge to improve matching robustness. The width ROIw of the ROI is defined by leaving large borders E1, E2 of, for instance, 32 pixels lying on each side of the image Ik for reducing the pin-cushion distortion. The borders E1, E2 must be large enough in relation with ROIh and with a further defined possible maximum shift amplitude Smax in order to ensure that the ROI, in image Ik or in image Ik+1 after shift, does not include the image intensifier border IIb, which would induce a strong bias. In an image of 512 pixels, ROIw=448 pixels for example.

Referring to FIG. 4B, the ROI is regularly divided into an integer number b of Reference Blocks Bj, where number j is an integer from 1 to b. Preferably, the reference blocks Bj are overlapping blocks to improve robustness. The overlapping ratio may be chosen to be ⅔, i.e. two thirds of a block surface are overlapped by their neighbors. The width Bw of the reference blocks Bj is preferably not smaller than 30–40 pixels because too small blocks contain too little information and may yield an unreliable match. On the other hand, in order to correct parallax, the width Bw should be small enough to avoid a block Bj covering several anatomical structures. A value of 42 pixels as block width Bw was found to be a good compromise between robustness and accuracy in images of 512 pixels.

Referring to FIG. 1C, preferably a sub-sampling operation 22 is applied to the original images of the sequence 11, by adding the image columns, for example, in groups of 4 in the direction x of the rows, thus providing a sequence of sub-sampled images 21, which presents the advantage to be smoothed relative to the original images. However, this smoothing must not be too strong so as not to remove small details, such as thin vessels. Another advantage of the sub-sampling operation is that the computation time is reduced. The image sequence 21 may be further processed by the matching operation 20.

Referring to FIGS. 5A and 5B, in the matching step 20, which will be called semi-elastic matching step whereafter, a shift value is estimated for the ROI block and for each of the reference blocks Bj of the ROI block. Thus, a so-called elasticity in the x-axis direction is provided, due to the fact that the different shift values estimated for the different reference blocks along the x axis are taken into account together with the shift value for the ROI block. A resolution for shift estimation is determined by the total number b of reference blocks Bj disposed along the x-axis in the ROI block. The whole shift for a sub-sequence of k+1 images comprising k image pairs is then fully defined by the values of j and k and is denoted S(k, j). In a variant called fully elastic matching operation, the ROI may further be divided into a number c of blocks along the y-axis. So the resolution for shift estimation is determined by the number of reference blocks along x and y axes. The whole shift for a sub-sequence of images is then fully defined by the values of k, j and i, where i is the number of blocks along the y axis, and is denoted S(k, j, i), with $1 \leq i \leq c$.

The semi-elastic matching operation roughly improves image quality by dividing the ROI into blocks Bj and, therefore, taking their different apparent motions into account. This operation has been tested with respect to the fully elastic matching operation and appears to be most suitable to solve the problems as exposed previously. The fully elastic operation presents a better resolution but is less robust than the semi-elastic operation. So the semi-elastic operation will be described hereafter in detail. Those skilled in the art may derive the fully elastic operation from the semi-elastic operation.

In the semi-elastic operation 20, the aim is to arrange of shift values equally distributed in the images. To this end, a block-matching technique based on gray values and on a similarity criterion is preferably used to match each block previously defined in the ROI independently. Several similarity criterions are known to those skilled in the art and may be used to estimate the block shifts between the two images of each image pair. Preferably in the semi-elastic operation, a criterion called Centered Cross-Correlation is used and denoted CC so that:

$$CC = \frac{\int f \cdot g - p \cdot \bar{f} \cdot \bar{g}}{\sqrt{(\int f^2 - p \cdot \bar{f}^2)(\int g^2 - p \cdot \bar{g}^2)}}, \quad (1)$$

with $$\bar{f} = \frac{1}{N} \cdot \int f. \quad (2)$$

This formula (1) permits of measuring the similarity between the gray value f(x,y) a block ROI or Bj at a position x, y on the x-axis in the first image Ik of a pair Pk, referred to as source image, and the gray value g(x+u, y+v) of a corresponding block in the second image Ik+1 of the pair, referred to as target image, said corresponding block being translated from (u,v) in said target image. In formula (1), $\bar{f}$ (2) is the mean gray value of the block. According to formula (1), $-1 \leq CC \leq 1$. This centered cross-correlation CC is invariant for an affine transformation of gray values. So, an affine variation of contrast between source and target images does not affect the result of CC.

The CC formula (1) is derived from a Cross-Correlation formula C (3) by subtracting the mean gray value $\bar{f}$ (2) from f. The formula C (3) is written as:

$$C = \frac{\int f \cdot g}{\sqrt{\int f^2 \cdot \int g^2}}. \tag{3}$$

Criterions C (3) and CC (1) give similar results as long as the blocks contain enough information or contrast. However, for small blocks containing poorly contrasted structures, such as small vessels in a uniform background, CC is preferred, because by removing the mean value, the continuous component is removed and the high spatial frequencies are enhanced i.e. small details. For the same reason, criterion CC is more sensitive to noise, but this problem is solved by using the sub-sampling sub-step 22.

In the matching operation 20, for the ROI block and for reference blocks Bj situated in the source image Ik of an image pair Pk, correlated blocks are searched in the target image Ik+1. For performing this search, CC values are calculated for all blocks of the target image Ik+1, situated at the same location on the x-axis (u=0 in CC formula (3)) and translated pixel after pixel along the y-axis of a number n of shift values (v in CC formula (3)), from 0 pixel to a maximum shift value Smax pixels, such as, for example, Smax=100 pixels (n=100) for peripheral angiography of the legs, Smax=64 pixels (n=64) for spine images. It is to be noted that the ROI height ROIh is chosen so that ROIh ≦Smax.

Said matching operation 20 is first performed on the ROI blocks comprising a calculation of the CC values for n predetermined values of v=S(k), from v=0 pixel to v=Smax, for each image pair Pk from k=1 to k=p, thus forming one curve CC versus S(k) for each pair. This provides a first output of the matching operation 20, which is a 2-D array 24 denoted SROI(nS, k), where (nS) is a first dimension for the n shift values S(k) from 0 to Smax pixels and where (k) is a second dimension for the number 1 to p of image pairs Pk.

Said matching operation 20 is further performed for the Bj reference blocks and comprises the calculation of the CC values for the n values of v=S(k, j), from v=0 pixel to v=Smax, for all blocks Bj from j=1 to j=b, and for all pairs Pk from k=1 to k=p, forming corresponding curves CC. This provides a second output of the matching operation 20, which is a 3-D array 25 denoted SB(nS, k, j), where (nS) is a first dimension for the n shift values S(k) from 0 to Smax pixels, where j is a second dimension for the number 1 to b of reference blocks Bj, and where (k) is a third dimension for the number 1 to p of image pairs.

FIGS. 7A to 7C show examples of curves of CC values versus shift amplitude values v=S(k). In FIGS. 7A and 7C, a substantially wide maximum of the CC curve is obtained with CC values close to 1 from the matching operation of a ROI block in one image pair Pk1, or Pk3, containing vertical structures such as tibia, fibula or a uniform background. In FIG. 7B, a CC curve shows a sharper peak of smaller value obtained from a ROI block in an image pair Pk2 that contains structures parallel with the x-axis such as knees, or ankles. Thus, it is to be noted that the maximum CC curve value gives little information about matching reliability, whereas the form of the CC curve indicates whether the matching is poorly reliable (FIG. 7A, 7C) or highly reliable (FIG. 7B), which is important for robustness.

The processing method aims at providing the best shift amplitude for each reference block and for the ROI block in each pair Pk. To this end, in step 3, a regularization operation is performed to give automatically, without visual intervention, a larger weight to reliably matched areas, such as knees compared to areas containing vertical structures, such as tibias. In this regularization step 3, a cost function is optimized for all the CC curves of the whole image sequence using a dynamic programming technique applied to:

a first sub-step 30a of regularization along the y-axis for determining the optimum ROI shift amplitude denoted OPTSROI(k) to match the ROI block in each image pair Pk along the image sequence; the input is the 2-D array SROI(nS, k) and the output is a 1D array, denoted OPTSROI(k);

a second sub-step 30b of regularization along the x-axis for determining the optimum block shift amplitude to match all the reference blocks Bj of the ROI block, in each image pair Pk, using said OPTSROI(k); the inputs are the 3-D array SB(nS, k, j) and the 1D array OPTSROI(k) and the output is a 2-D array denoted OPTSB(k, j).

Figure 8:
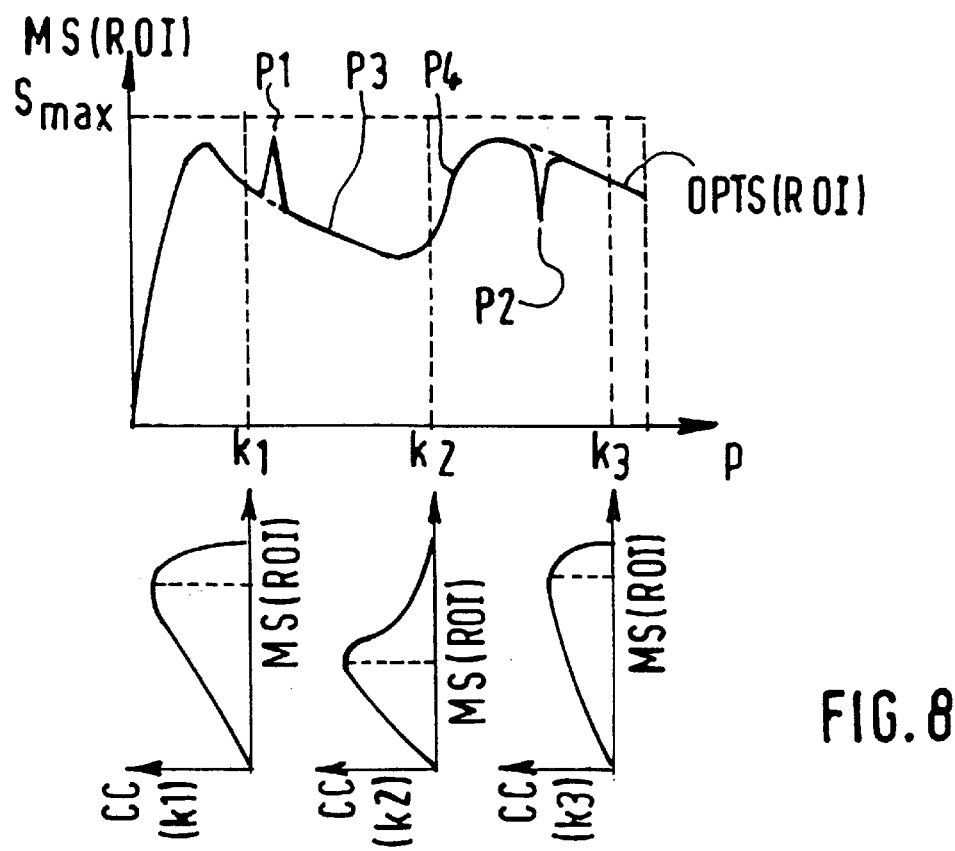
FIG. 8 shows a curve of the ROI optimum shift amplitude versus the pair number.

Referring to FIG. 8, in the first sub-step 30a of regularization along the y-axis, shift amplitudes, which are denoted MS(ROI) and referred to as best shift values, and which correspond to the maximum CC values of all the CC curves related to the ROI blocks, are determined first. Then a curve of said best shift values MS(ROI) versus the image pair number k, with k from 1 to p, is calculated. As shown on FIG. 8, this curve MS(ROI) may show sharp peaks P1, P2 corresponding to parallax artifacts. Sub-step 30a consists in regularizing said curve MS(ROI) by eliminating aberrant shift values, such as P1, P2, by using a cost finction which applies high costs to such peaks. This cost function evaluation includes a local cost function LC(S) and a transition cost function TC(δS) evaluation giving matching costs for each shift and costs to move from one shift value to another shift value in the next image pair, respectively.

For evaluating the local cost function LC(S), the matching criterion CC may be used, where the variable v=S is the best shift amplitude MS(ROI), from 0 to Smax pixels:

$$LC(S) = (1/2)[1 - CC(S)] \text{ with } 0 \leq LC(S) \leq 1 \tag{4a}$$

Figure 9A:
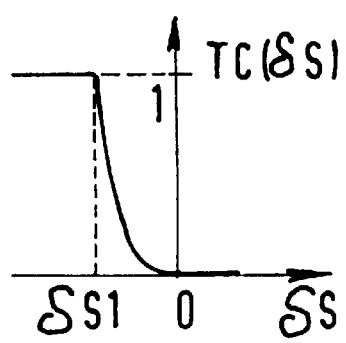
FIGS. 9A, 9B show curves of transition cost TC($\delta$S) in regularization along y.
Figure 9B:
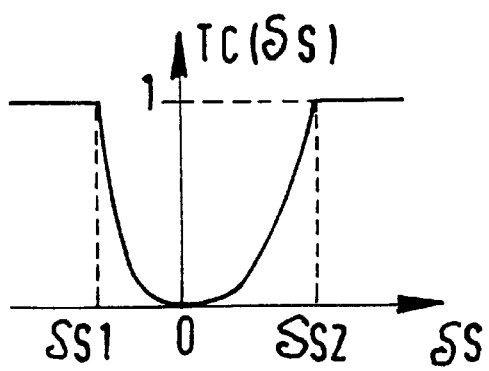

For evaluating the transition cost function TC(δS), a stationary function may be used which is independent of the image pair number k and which depends only on the difference of shift denoted δS between the shifts of consecutive image pairs Pk, Pk+1. Thus, TC(δS) is the cost to go from the best shift value MS(ROI) for an image pair Pk to the best shift value MS(ROI) for a subsequent image pair Pk+1. First and second threshold values δS1 and δS2 are defined for the shift difference δS such as: δS1<0, δS2>0, so that:

$$TC(\delta S) = 1 \text{ for } \delta S \leq \delta S1 \text{ and for } \delta S2 \leq \delta S \tag{5a}$$

$$TC(\delta S) = (\delta S/\delta S1)^Q \text{ for } \delta S1 \leq \delta S \leq 0 \tag{5b}$$

$$TC(\delta S) = (\delta S/\delta S2)^Q \text{ for } 0 \leq \delta S \leq \delta S2 \tag{5c}$$

illustrated by the curve of FIG. 9B, with the exponent Q>0, for instance Q=4.

The regularization provides the most regular path OPTS (ROI) formed by the optimum shift amplitudes for the image pairs, by minimizing a global cost function GC:

$$GC = \min_p \sum [\lambda LC(S) + TC(\delta S)] \quad (6)$$

where λ is a weight parameter which defines the balance between local and transition costs. For a high λ value, little regularization will be made, and for a small λ value, the regularization has a heavier weight and fits a horizontal line in the 2-D graph of FIG. 8.

The equation (6) may be solved using the Viterbi algorithm as described, for instance, in the publication "An Introduction to Hidden Markov Models" by L. R. Rabiner and B. H. Juang in IEEE ASSP MAGAZINE, JANUARY 1986, p. 11, BOX 2.

Figure 10A:
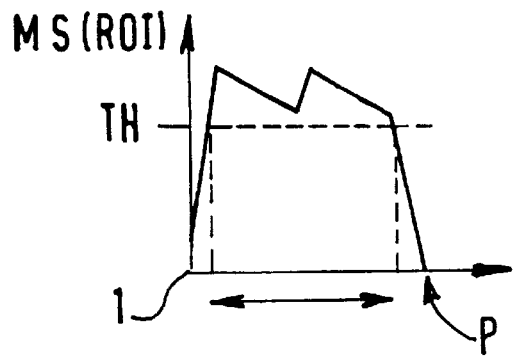
FIGS. 10A, 10B show best shift amplitude curves.
Figure 10B:
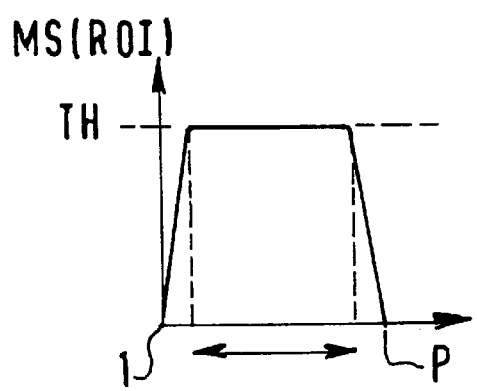

For choosing the right parameters for the regularization sub-step 30a, prior knowledge about the acquisition profile is needed, which is application dependent. In fact, this profile MS(ROI) for peripheral angiography is irregular as shown in FIG. 10A or 8, because the image acquisition must follow an irregular propagation 130 of a contrast fluid in the leg arteries, so that the patient table motion is not constant, whereas this profile for spine acquisition, as shown in FIG. 10B, is more constant. Transition cost has thus to be defined in each case, whereas local cost remains the same. First of all, strong acceleration and deceleration are found at each extremity of these curves of FIGS. 10A, 10B. Thus, a shift threshold TH is defined for limiting the part of the curve MS(ROI) to be regularized.

In the case of spine acquisition, the transition cost given by equations 5a to 5c may be used in relation to FIG. 9B. In the case of peripheral angiography, the profile of FIG. 10A shows a deceleration part P3 and an acceleration part P4. In the transition cost equation, formula (5c) may be replaced by the following formula (5d) with reference to FIG. 9A:

$$TC(\delta S) = 0 \text{ for } 0 \leq \delta S \text{ and } \delta S2 = +\infty \quad (5d)$$

Thus, a substantially large acceleration, such as P4, is allowed by zero cost, a small deceleration such as P5 is permitted while a sudden deceleration is heavily weighted. So, transition cost of equations (5a, b, d)) penalizes isolated decelerations associated to peaks such as P1, P2 and regularizes the MS(ROI) profile to provide a profile OPTS(ROI).

A regularization sub-step 30b is further performed along the x-axis in the b blocks defined in the ROI block of each image while the same method is used. Shift amplitudes, which are denoted MS(B) and referred to as best shift values and which correspond to the maximum CC values of all CC curves related to the Bj blocks associated to the ROI block in an image pair Pk, are determined first. A curve similar to the curve of FIG. 8 is calculated from said best shift values MS(B) versus the Bj block number j from 1 to b (not represented).

Local cost is also used as defined by equation (4a), where the variable k will be replaced by j, with 1≤j≤b. From the previous regularization of the ROI shift along the y-axis in the p image pairs, prior knowledge about an optimum shift value for the associated ROI block has been obtained. So, said prior knowledge, referred to as PC(S), is added to the CC formula used to define this local cost, specifying that the shift amplitudes for Bj and ROI blocks should be substantially equal and result in the following local cost equation (4b), where the variable S is now the best shift value MS(B):

$$LC(S) = (1/2)[1 - CC'(S)], \text{ with } CC'(S) = CC(S) + PC(S) \quad (4b)$$

$$\text{where } PC(S) = -\mu[S - OPTS(ROI)]^V/[Hw]^V, \text{ for } S - OPTS(ROI) \leq Sw \quad (7a)$$

$$\text{and } PC(S) = -1 \text{ for } S - OPTS(ROI) > Sw \quad (7b)$$

where μ is a positive scaling factor defining the prior knowledge function weight, MS(B) is the block shift value, OPTS(ROI) is the ROI shift and 2Sw defines the range of possible shifts around OPTS(ROI). The width Sw=WP. OPTS(ROI)/2, with WP so that 0≤WP≤1.

Figure 11A:
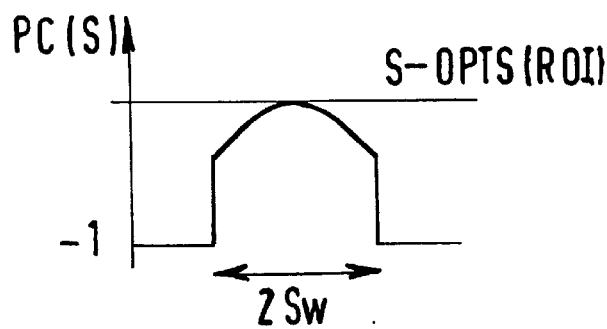
FIG. 11A shows a curve of prior knowledge and FIG. 11B a curve of transition cost TC($\delta$S) in regularization along x.

The ratio MS(B)/OPTS(ROI) is the ratio between the actual distance of the object seen in the block and the focal distance. An object may be seen at any distance within this possible range with the same probability, thus the function has to be substantially flat, which may be obtained, for example, by using the exponent V=4. FIG. 11A represents the function PC(S) versus MS(B) which has to be centered on each block Bj. The local cost LC(S) is improved by taking into account that CC curve profiles vary from one block to another, by adapting the prior knowledge function weight μ by using small or larger weight μ when the block contains reliable or poor information respectively.

Figure 11B:
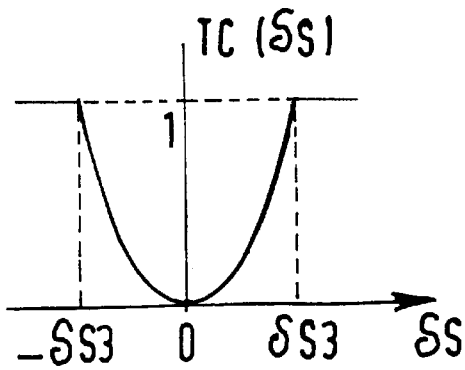

Referring to FIG. 11B, transition cost TC(δS) is also estimated using a symmetrical function where δS3 is a positive constant:

Setting δS=MS(Bj+1)−MS(Bj) (8)

$$TC(\delta S) = (|\delta S|/\delta S3)^U \text{ for } |\delta S| \leq \delta S3 \quad (9a)$$

$$TC(\delta S) = 1 \text{ for } -\delta S3 \leq |\delta S| \quad (9b)$$

where TC(δS) is the cost to go from the shift value MS(Bj) in block Bj to the shift value MS(Bj+1) in the next block Bj+1. For reasons already discussed, the exponent U=4 is preferred. The difference of best shift values between two neighboring blocks has flat probability between the range of possible values. The constant δS3 is defined by:

δS3=SP·OPTS(ROI), where SP is a positive parameter: 0≤SP≤1.

The further step 4 is the reconstruction of the overview image 41 performed on the original image. To this end a sub-step of expansion 42 is performed to interpolate the results of the regularization step obtained on the sub-sampled images including borders E1, E2 and comprising, for instance, 32 Bj blocks to a full image-width denoted Iw of, for example, 512 pixels. The input of the expansion sub-step 42 is the 2-D array OPTS[B(j,k)] which gives the optimum shift value calculated on each block, and the output is a 2-D array OPTS[B(Iw,p)] which gives the optimum shift value interpolated for each column along the image width Iw.

Figure 12A:
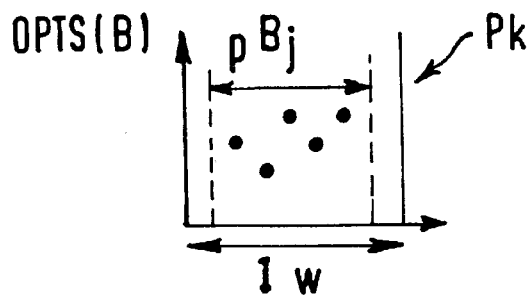
FIGS. 12A, 12B illustrate the interpolation step for reference blocks.
Figure 12B:
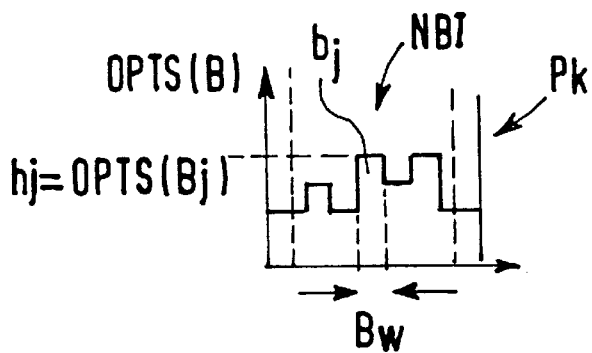

Referring to FIG. 12A and FIG. 12B, an interpolation method referred to as NBI Nearest Block Interpolation is then preferred, even though it may lead to visible block effect. As the blocks are overlapping, when a structure overlaps two contiguous blocks having different shifts, the block effect will be visible and cannot lead to an ambiguous diagnosis.

Figure 13:
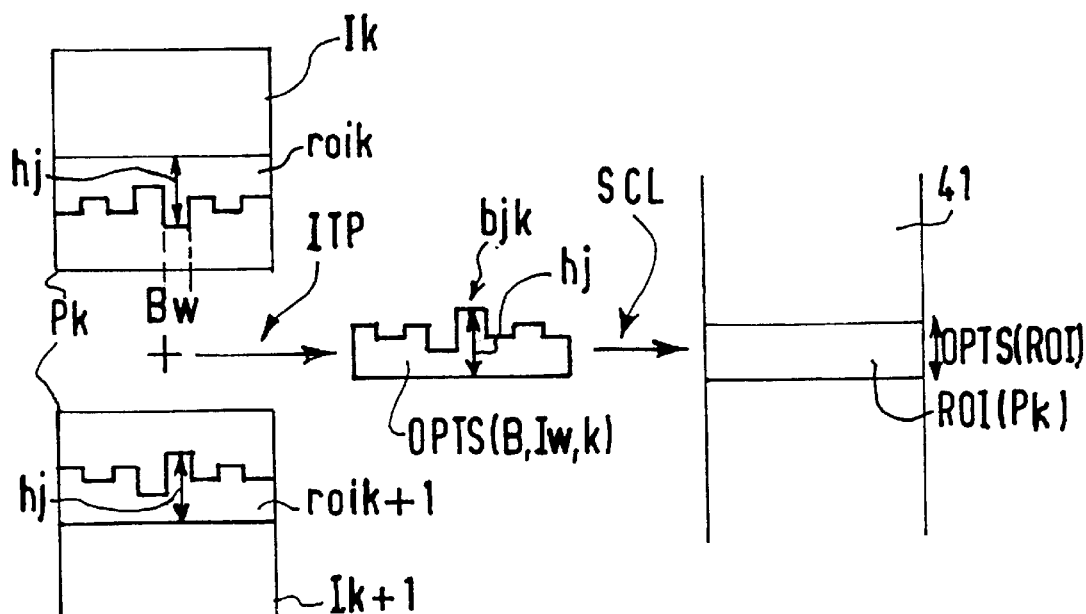
FIG. 13 illustrates the reconstruction step from ROI and block shifts.

Referring to FIG. 13, for each block Bj two symmetrical sub-blocks denoted bj having the Bj block-width Bw are defined in the images Ik, Ik+1. The height denoted hj of each sub-block bj is given by the individual optimum block shift value OPTS(B) for the associated Bj block. Then, in the images Ik and Ik+1, two symmetrical strips denoted roik and roik+1 are formed from said sub-blocks bj, the height of said strips varying with the height hj of the bj sub-blocks along the x-axis. An interpolation operation denoted ITP is applied to the gray levels of the symmetrical sub-blocks bj in image pairs Pk to form resulting interpolated sub-blocks denoted bjk. To this end, linearly decreasing and increasing weight factors are applied along the y-axis to the gray levels of the said sub-blocks bj in images of a pair Pk, and then the weighted gray levels are added to form the interpolated sub-blocks bjk. In a pair Pk, all the interpolated sub-blocks bjk are associated to provide a resulting strip denoted OPTS(B,Iw,k), wherein each interpolated sub-block bjk of different height hj is submitted to a scaling operation of expansion or compression denoted SCL according to a common height which is OPTS(ROI) providing a strip denoted ROI(Pk). These operations ITP+SCL are performed for all pairs Pk. All the strips ROI(Pk) thus obtained are combined to form the overview image 41. Therefore, the input of the reconstruction step 4 is the 1-D array OPTS (ROI), which gives the optimum shift value of ROI for each image pair Pk, and the 2-D array OPTS(B,Iw, k), which gives the shift value for each pixel column. The output is a 1D array OPTS[ROI(Pk)] for reconstructing the overview image 41.

All references cited herein, as well as the priority document European Patent Application 99400399.4 filed Feb. 18, 1999, are incorporated herein by reference in their entirety and for all purposes to the same extent as if each individual publication or patent or patent application was specifically and individually indicated to be incorporated by reference in its entirety for all purposes.

What is claimed is:

1. An image processing method comprising:
   acquiring a sequence of overlapping images representing an elongated scene, said images being obtained at different positions along a translation direction, and
   merging said images into an overview image, said merging further including:
   determining regularized displacement fields of overlapping regions of interest and sections of said regions in image pairs, and
   merging said sections based on dimensions calculated from the regularized region displacement field,
   wherein the sub-step of determining further comprises:
   determining the regions and the region sections that have first dimensions suitable for matching in image pairs and estimating region and section displacement fields, and
   regularizing said region and section displacement fields.

2. A method as claimed in claim 1, wherein the sub-step of merging further comprises:
   determining sections in said image pairs that have second dimensions suitable for merging, calculated from the regularized section displacement field,
   interpolating pixel values of said sections so as to evaluate pixel values of regions in the corresponding pairs,
   scaling said sections in the regions with dimensions calculated from the regularized region displacement field, and
   reconstructing the overview image with said regions.

3. A method as claimed in claim 2, wherein the sections are regular region divisions which form overlapping blocks having the same height as the corresponding regions.

4. A method as claimed in claim 3, wherein the displacement fields are determined by a matching operation using a similarity criterion applied to the pixel values of said regions and sections respectively over a predetermined range of possible shift values and over all image pairs of the sequence.

5. A method as claimed in claim 4, wherein the matching operation provides for said regions a 2-D array of the criterion values in a first dimension for the number of possible shift values and a second dimension for the number of image pairs in the image sequence and provides for said sections a 3-D array of criterion values in a first dimension for the number of possible shift values, a second dimension for the number of sections per region and a third dimension for the number of image pairs in the image sequence.

6. A method as claimed in claim 5, wherein the step of regularizing further comprises applying first and second regularization operations to said 2-D and 3-D arrays respectively to provide the regularized displacement fields by estimating optimum shift values for the regions from best shift values determined for said regions over the sequence of images and by estimating optimum shift values for the sections from best shift values determined for said sections over the regions where they are defined and over the sequence of images.

7. A method as claimed in claim 6, wherein the regularization operations provide for the regions a 1-D array of optimum shift values corresponding to maximum criterion values in a dimension for the number of image pairs, and provide for the sections a 2-D array of optimum shift values corresponding to maximum criterion values in a first dimension for the number of sections per region and a second dimension for the number of image pairs.

8. A method as claimed in claim 7, wherein the regularization operations are performed using a cost function which penalizes aberrant variations of said best shift values.

9. A method as claimed in claim 8, wherein the cost function is carried out in a first regularization operation of the region displacement fields by minimizing a first global cost function over the number of image pairs in the sequence and in a second regularization operation of the section displacement field by minimizing a second global cost function over the number of sections per region.

10. A method as claimed in claim 9, wherein the global cost functions are defined as a linear combination of a transition cost and of a local cost weighted by a weight parameter which defines the balance between the transition cost and the local cost.

11. A method as claimed in claim 10, wherein in the cost function for regularizing the region displacement field, the local cost is the cost for each shift in an image pair, and the transition cost is the cost to move from one shift value for one image pair to another shift value for a consecutive image pair and a prior knowledge of the acquisition profile is taken into account for evaluating said transition cost.

12. A method as claimed in claim 11, wherein, in the cost function for regularizing the section displacement field, the local cost is the cost for each section shift in an image pair and a prior knowledge of the optimum shift value for the region where the sections are defined is taken into account for evaluating said local cost, and the transition cost is the cost to move from one shift value for one section to another shift value for a consecutive section.

13. A method as claimed in claim 4, wherein the similarity criterion is a Centered Cross-Correlated function or a Cross-Correlated function applied to pixel values.

14. A method as claimed in claim 3, further comprising applying a sub-sampling operation to the sequence images before the matching operation by adding columns of individual images in groups, and performing an expansion operation before the reconstruction operation for carrying out said reconstruction operation on the original dimensions of said images.

15. An image processing system comprising:
   means for acquiring a sequence of overlapping images representing an elongated scene, said images being obtained at different positions along a translation direction, and means for merging said images into an overview image, said means for merging further including:
  means for determining regularized displacement fields of overlapping regions of interest and sections of said regions in image pairs, and
  means for merging said sections based on dimensions calculated from the regularized region displacement field,
wherein the means for determining further comprises:
  means for determining the regions and the region sections that have first dimensions suitable for matching in image pairs and estimating region and section displacement fields, and
  means for regularizing said region and section displacement fields.

16. The image processing system as claimed in claim 15, wherein the sub-step of merging further comprises:
  means for determining sections in said image pairs that have second dimensions suitable for merging, calculated from the regularized section displacement field,
  means for interpolating pixel values of said sections so as to evaluate pixel values of regions in the corresponding pairs,
  means for scaling said sections in the regions with dimensions calculated from the regularized region displacement field, and
  means for reconstructing the overview image with said regions.

17. A medical apparatus comprising:
  acquisition means for acquiring examination images of a patient,
  translation means for acquiring translation of consecutive overlapping images of an elongated part of the patient, and
  an image processing system comprising:
    means for acquiring a sequence of overlapping images representing an elongated scene, said images being obtained at different positions along a translation direction, and
  means for merging said images into an overview image, said merging further including:
    means for determining regularized displacement fields of overlapping regions of interest and sections of said regions in image pairs, and
    means for merging said sections based on dimensions calculated from the regularized region displacement field, and
  wherein the means for determining further comprises:
    means for determining the regions and the region sections that have first dimensions suitable for matching in image pairs and estimating region and section displacement fields, and
    means for regularizing said region and section displacement fields.

18. An apparatus as claimed in claim 17, wherein the sub-step of merging further comprises:
  means for determining sections in said image pairs that have second dimensions suitable for merging, calculated from the regularized section displacement field,
  means for interpolating pixel values of said sections so as to evaluate pixel values of regions in the corresponding pairs,
  means for scaling said sections in the regions with dimensions calculated from the regularized region displacement field, and
  means for reconstructing the overview image with said regions.

* * * * *